(12) United States Patent
Vainauskas et al.

(10) Patent No.: US 12,312,610 B2
(45) Date of Patent: May 27, 2025

(54) VACCINIA CAPPING ENZYME COMPOSITIONS AND METHODS

(71) Applicant: New England Biolabs, Inc., Ipswich, MA (US)

(72) Inventors: Saulius Vainauskas, Newburyport, MA (US); Siu-hong Chan, Ipswich, MA (US); Christopher H. Taron, Essex, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 18/462,868

(22) Filed: Sep. 7, 2023

(65) Prior Publication Data

US 2023/0416701 A1    Dec. 28, 2023

Related U.S. Application Data

(62) Division of application No. 17/348,127, filed on Jun. 15, 2021, now Pat. No. 11,788,074.

(60) Provisional application No. 63/042,939, filed on Jun. 23, 2020.

(51) Int. Cl.
| | | |
|---|---|---|
| C12N 9/12 | (2006.01) | |
| C12N 15/81 | (2006.01) | |
| C12R 1/84 | (2006.01) | |

(52) U.S. Cl.
CPC .......... *C12N 9/1241* (2013.01); *C12N 15/815* (2013.01); *C07K 2319/00* (2013.01); *C12R 2001/84* (2021.05); *C12Y 207/0705* (2013.01)

(58) Field of Classification Search
None
See application file for complete search history.

(56) References Cited

U.S. PATENT DOCUMENTS

| | | |
|---|---|---|
| 8,846,348 B2 | 9/2014 | Jendrisak et al. |
| 8,962,292 B2 | 2/2015 | Jais |
| 9,005,930 B2 | 4/2015 | Jendrisak et al. |
| 9,115,380 B2 | 8/2015 | Jendrisak et al. |
| 9,512,456 B2 | 12/2016 | Wang et al. |
| 9,540,671 B2 | 1/2017 | Jais |
| 9,629,804 B2 | 4/2017 | Heartlein et al. |
| 9,790,531 B2 | 10/2017 | Wang et al. |
| 10,093,915 B2 | 10/2018 | Wu et al. |
| 10,428,368 B2 | 10/2019 | Schildkraut et al. |
| 10,519,431 B2 | 12/2019 | Ong et al. |
| 11,788,074 B2 | 10/2023 | Vainauskas et al. |
| 2012/0251618 A1 | 10/2012 | Schrum et al. |
| 2013/0042334 A1 | 2/2013 | Eukarys |
| 2014/0152211 A1 | 6/2014 | Ko |
| 2016/0038432 A1 | 2/2016 | DeRosa et al. |
| 2017/0253911 A1 | 9/2017 | Schildkraut et al. |
| 2018/0195061 A1 | 7/2018 | Schildkraut et al. |
| 2018/0237817 A1 | 8/2018 | Roos et al. |

FOREIGN PATENT DOCUMENTS

| | | |
|---|---|---|
| AU | 2007238624 B2 | 5/2012 |
| EP | 2010659 B1 | 1/2009 |
| EP | 2558579 B1 | 8/2013 |
| EP | 3077406 B1 | 7/2019 |
| WO | 2017123748 A1 | 7/2017 |
| WO | 2018236617 A1 | 12/2018 |
| WO | 2019020811 A1 | 1/2019 |

OTHER PUBLICATIONS

Cong, et al (1993). "Covalent catalysis in nucleotidyl transfer. A KTDG motif essential for enzyme-GMP complex formation by mRNA capping enzyme is conserved at the active sites of RNA and DNA ligases." J Biol Chem 268(10): 7256-60.
Niles, et al (1993). "Identification of the vaccinia virus mRNA guanyltransferase active site lysine." J Biol Chem 268(33): 24986-9.
Higman, et al (1994). "Location of the S-adenosyl-L-methionine binding region of the vaccinia virus mRNA (guanine-7-)methyltransferase." J Biol Chem 269(21): 14982-7.
Mao, et al (1994). "Intrinsic RNA (guanine-7) methyltransferase activity of the vaccinia virus capping enzyme D1 subunit is stimulated by the D12 subunit. Identification of amino acid residues in the D1 protein required for subunit association and methyl group transfer." J Biol Chem 269(39): 24472-9.
Gong, et al (2003). "Mapping the active site of vaccinia virus RNA triphosphatase." Virology 309(1): 125-34.
Higman, et al (1992). "The vaccinia virus mRNA (guanine-N-7-)-methyltransferase requires both subunits of the mRNA capping enzyme for activity." J Biol Chem 267(23): 16430-7.
Higman, et al. (1994). "The mRNA (guanine-7) methyltransferase domain of the vaccinia virus mRNA capping enzyme. Expression in *Escherichia coli* and structural and kinetic comparison to the intact capping enzyme." J Biol Chem 269(21): 14974-81.
Osborn, et al., A picornaviral 2A-like sequence-based tricistronic vector allowing for high-level therapeutic gene expression coupled to a dual-reporter system. Mol Ther. 2005; 12:569-574.
Donnelly, et al Analysis of the aphthovirus 2A/2B polyprotein 'cleavage' mechanism indicates not a proteolytic reaction, but a novel translational effect: a putative ribosomal 'skip' J Gen Virol. 2001; 82:1013-1025.
Donnelly, et al., The 'cleavage' activities of foot-and-mouth disease virus 2A site-directed mutants and naturally occurring '2A-like' sequences. J Gen Virol. 2001; 82:1027-1041. doi: 10.1099/0022-1317-82-5-1027.
Lee, et al., Synergistic effects of 2A-mediated polyproteins on the production of lignocellulose degradation enzymes in tobacco plants. J Exp Bot. 2012; 63:4797-4810.
Rasala, et al. (2012). Robust expression and secretion of Xylanase1 in Chlamydomonas reinhardtii by fusion to a selection gene and processing with the FMDV 2A peptide. PLoS One. 7:e43349.

(Continued)

*Primary Examiner* — Richard G Hutson
(74) *Attorney, Agent, or Firm* — New England Biolabs, Inc

(57) ABSTRACT

The present disclosure relates, according to some embodiments, to compositions, methods, and/or kits for producing vaccinia capping enzyme. For example, active, heterodimers of vaccinia capping enzyme may be produced as fusions comprising D1 and D12 subunits. Vaccinia capping enzyme fusion proteins may further comprise a linker.

14 Claims, 4 Drawing Sheets

Specification includes a Sequence Listing.

(56) References Cited

OTHER PUBLICATIONS

Chng, et al., (2015). Cleavage efficient 2A peptides for high level monoclonal antibody expression in CHO cells. MAbs. 7:403-412.
Sun, et al. (2012). Double Candida antarctica lipase B co-display on Pichia pastoris cell surface based on a self-processing foot-and-mouth disease virus 2A peptide. Appl Microbiol Biotechnol. 96:1539-1550.
De Amorim Araujo, et al., (2015). Coexpression of cellulases in Pichia pastoris as a self-processing protein fusion. AMB Express, 5(1), 84.
De Felipe, et al. (2003). Co-translational, intraribosomal cleavage of polypeptides by the foot-and-mouth disease virus 2A peptide. J Chem. 278:11441-11448.
Crasto, et al. (2000). Linker: a program to generate linker sequences for fusion proteins. Protein engineering, 13(5), 309-312.
Wu, et al. (2004). High efficiency transformation by electroporation of Pichia pastoris pretreated with lithium acetate and dithiothreitol. BioTechniques, 36(1), 152-154.
Looke, et al.,(2011). Extraction of genomic DNA from yeasts for PCR-based applications. BioTechniques, 50(5), 325-328.
Ryan, et. al., 1991, Cleavage of foot-and-mouth disease virus polyprotein is mediated by residues located within a 19 amino acid sequence. J Gen Virol. 72:2727-2732.
Shuman, The Journal of Biological Chemistry, 265, 20, 11960-11966, 1990.
Fuchs, et al., RNA, 22, 1454-1466, 2016.
Benarroch, et al., Structure, 16, 201-512, 2008.
Shuman, JBC, 265, 20, 11960-11966, 1990.
Guo, et al., Proc Natl Acad Sci USA. 87, 11:4023-7, 1990.
Paoletti, et al., Journal of Virology, 33, 1, 208-19, 1980.
Furuichi, et al., Nature, 266, 235-237, 1977.
Lewis, et al., Eur. J. Biochem. 247, 461-469, 1977.
Iizuka, et al., Mol. Cell. Biol. 14, 7322-7330, 1994.
Rubenstein, et al., JCB, 96, 1464-1469, 1983.
Shuman, Methods in Enzymology, 181, 170-180, 1990.
Benamar, et al., Frontiers in Microbiology, 7, 3, 2016.
Du, et al., Journal of Virology, 95, 5, e02029-20, 2021.
Dunyak, et al., Eukaryotic Cell, 1, 6, 1010-1020, 2002.
Hausmann, et al., The Journal of Biological Chemistry, 277, 1, 96-103, 2022.
Jais, et al., Nucleic Acids Research, 47, 5, 2681-2698, 2019.
Pena, et al., Virology, 193, 319-328, 1993.
Reteno, et al., Journal of Virology, 89, 13, 6585-6594, 2015.
Schneider, et al., Molecular and Cellular Biology, 30, 2353-2364, 2010.
Takizawa, et al., PLoS ONE, 8, 10, e78000, 2013.
Johnson, et al., bioRxiv 2023.03.04.531015; doi: https://doi.org/10.1101/2023.03.04.531015.
Fisher, et al., ACS Cent. Sci. 2019, 5, 1844-1856.
Uniprot A01142BZT8 version 11 dated Jul. 31, 2019.
Uniprot A0A142BZT8.A0 A142BZT8_9VIRU, Jun. 8, 2016.
Beverly, et al., Analytical and Bioanalytical Chemistry, 408, 5021-2030, 2016.
Wulf, et al., Scientific Reports, 9, 8594, 2019.
Pichlmair, et al., Science 2006 314: 997-1001.
Diamond, et al., Cytokine & Growth Factor Reviews, 2014 25: 543-550.
Li, et al J. Org. Chem. 2012 77: 9889-9892.
Cong, et al, Molecular and Cellular Biology, 6222-6231, 15, 11, 1995.
New England Biolabs, M2080 Capping System product information Feb. 26, 2020.

SEQUENCE LISTING

```
Sequence total quantity: 8
SEQ ID NO: 1              moltype = AA  length = 867
FEATURE                   Location/Qualifiers
REGION                    1..867
                          note = Synthetic construct
REGION                    1..867
                          note = MISC_FEATURE - D1 Polypeptide
source                    1..867
                          mol_type = protein
                          organism = synthetic construct
SEQUENCE: 1
MGHHHHHHHH HHSSGHIEGR HRSMDANVVS SSTIATYIDA LAKNASELEQ RSTAYEINNE    60
LELVFIKPPL ITLTNVVNIS TIQESFIRFT VTNKEGVKIR TKIPLSKVHG LDVKNVQLVD   120
AIDNIVWEKK SLVTENRLHK ECLLRLSTEE RHIFLDYKKY GSSIRLELVN LIQAKTKNFT   180
IDFKLKYFLG SGAQSKSSLL HAINHPKSRP NTSLEIEFTP RDNETVPYDE LIKELTTLSR   240
HIFMASPENV ILSPPINAPI KTFMLPKQDI VGLDLENLYA VTKTDGIPIT IRVTSNGLYC   300
YFTHLGYIIR YPVKRIIDSE VVVFGEAVKD KNWTVYLIKL IEPVNAINDR LEESKYVESK   360
LVDICDRIVF KSKKYEGPFT TTSEVVDMLS TYLPKQPEGV ILFYSKGPKS NIDFKIKKEN   420
TIDQTANVVF RYMSSEPIIF GESSIFVEYK KFSNDKGFPK EYGSGKIVLY NGVNYLNNIY   480
CLEYINTHNE VGIKSVVVPI KFIAEFLVNG EILKPRIDKT MKYINSEDYY GNQHNIIVEH   540
LRDQSIKIGD IFNEDKLSDV GHQYANNDKF RLNPEVSYFT NKRTRGPLGI LSNYVKTLLI   600
SMYCSKTFLD DSNKRKVLAI DFGNGADLEK YFYGEIALLV ATDPDADAIA RGNERYNKLN   660
SGIKTKYYKF DYIQETIRSD TFVSSVREVF YFGKFNIIDW QFAIHYSFHP RHYATVMNNL   720
SELTASGGKV LITTMDGDKL SKLTDKKTFI IHKNLPSSEN YMSVEKIADD RIVVYNPSTM   780
STPMTEYIIK KNDIVRVFNE YGFVLVDNVD FATIIERSKK FINGASTMED RPSTRNFFEL   840
NRGAIKCEGL DVEDLLSYYV VYVFSKR                                      867

SEQ ID NO: 2              moltype = AA  length = 287
FEATURE                   Location/Qualifiers
REGION                    1..287
                          note = Synthetic construct
REGION                    1..287
                          note = MISC_FEATURE - D12 polypeptide
source                    1..287
                          mol_type = protein
                          organism = synthetic construct
SEQUENCE: 2
MDEIVKNIRE GTHVLLPFYE TLPELNLSLG KSPLPSLEYG ANYFLQISRV NDLNRMPTDM    60
LKLFTHDIML PESDLDKVYE ILKINSVKYY GRSTKADAVV ADLSARNKLF KRERDAIKSN   120
NHLTENNLYI SDYKMLTFDV FRPLPDFVNE KYCIIKLPTL FGRGVIDTMR IYCSLFKNVR   180
LLKCVSDSWL KDSAIMVASD VCKKNLDLFM SHVKSVTKSS SWKDVNSVQF SILNNPVDTE   240
FINKFLEFSN RVYEALYYVH SLLYSSMTSD SKSIENKHQR RLVKLLL                 287

SEQ ID NO: 3              moltype = AA  length = 33
FEATURE                   Location/Qualifiers
REGION                    1..33
                          note = Synthetic construct
REGION                    1..33
                          note = MISC_FEATURE - Linker 1D2A
source                    1..33
                          mol_type = protein
                          organism = synthetic construct
SEQUENCE: 3
EARHKQKIVA PVKQTLNFDL LKLAGDVESN PGP                                 33

SEQ ID NO: 4              moltype = AA  length = 1187
FEATURE                   Location/Qualifiers
REGION                    1..1187
                          note = Synthetic construct
REGION                    1..1187
                          note = MISC_FEATURE - D1-1D2A-D12 Polypeptide
REGION                    868..900
                          note = MISC_FEATURE - 1D2A linker
source                    1..1187
                          mol_type = protein
                          organism = synthetic construct
SEQUENCE: 4
MGHHHHHHHH HHSSGHIEGR HRSMDANVVS SSTIATYIDA LAKNASELEQ RSTAYEINNE    60
LELVFIKPPL ITLTNVVNIS TIQESFIRFT VTNKEGVKIR TKIPLSKVHG LDVKNVQLVD   120
AIDNIVWEKK SLVTENRLHK ECLLRLSTEE RHIFLDYKKY GSSIRLELVN LIQAKTKNFT   180
IDFKLKYFLG SGAQSKSSLL HAINHPKSRP NTSLEIEFTP RDNETVPYDE LIKELTTLSR   240
HIFMASPENV ILSPPINAPI KTFMLPKQDI VGLDLENLYA VTKTDGIPIT IRVTSNGLYC   300
YFTHLGYIIR YPVKRIIDSE VVVFGEAVKD KNWTVYLIKL IEPVNAINDR LEESKYVESK   360
LVDICDRIVF KSKKYEGPFT TTSEVVDMLS TYLPKQPEGV ILFYSKGPKS NIDFKIKKEN   420
TIDQTANVVF RYMSSEPIIF GESSIFVEYK KFSNDKGFPK EYGSGKIVLY NGVNYLNNIY   480
CLEYINTHNE VGIKSVVVPI KFIAEFLVNG EILKPRIDKT MKYINSEDYY GNQHNIIVEH   540
LRDQSIKIGD IFNEDKLSDV GHQYANNDKF RLNPEVSYFT NKRTRGPLGI LSNYVKTLLI   600
SMYCSKTFLD DSNKRKVLAI DFGNGADLEK YFYGEIALLV ATDPDADAIA RGNERYNKLN   660
```

```
SGIKTKYYKF DYIQETIRSD TFVSSVREVF YFGKFNIIDW QFAIHYSFHP RHYATVMNNL  720
SELTASGGKV LITTMDGDKL SKLTDKKTFI IHKNLPSSEN YMSVEKIADD RIVVYNPSTM  780
STPMTEYIIK KNDIVRVFNE YGFVLVDNVD FATIIERSKK FINGASTMED RPSTRNFFEL  840
NRGAIKCEGL DVEDLLSYYV VYVFSKREAR HKQKIVAPVK QTLNFDLLKL AGDVESNPGP  900
MDEIVKNIRE GTHVLLPFYE TLPELNLSLG KSPLPSLEYG ANYFLQISRV NDLNRMPTDM  960
LKLFTHDIML PESDLDKVYE ILKINSVKYY GRSTKADAVV ADLSARNKLF KRERDAIKSN  1020
NHLTENNLYI SDYKMLTFDV FRPLFDFVNE KYCIIKLPTL FGRGVIDTMR IYCSLFKNVR  1080
LLKCVSDSWL KDSAIMVASD VCKKNLDLFM SHVKSVTKSS SWKDVNSVQF SILNNPVDTE  1140
FINKFLEFSN RVYEALYYVH SLLYSSMTSD SKSIENKHQR RLVKLLL               1187

SEQ ID NO: 5              moltype = AA  length = 15
FEATURE                   Location/Qualifiers
REGION                    1..15
                          note = Synthetic construct
REGION                    1..15
                          note = MISC_FEATURE - Flexible Linker GS
source                    1..15
                          mol_type = protein
                          organism = synthetic construct
SEQUENCE: 5
GGGGSGGGGS GGGGS                                                  15

SEQ ID NO: 6              moltype = AA  length = 1169
FEATURE                   Location/Qualifiers
REGION                    1..1169
                          note = Synthetic construct
REGION                    1..1169
                          note = MISC_FEATURE - D1-GS-D12 Polypeptide
source                    1..1169
                          mol_type = protein
                          organism = synthetic construct
SEQUENCE: 6
MGHHHHHHHH HHSSGHIEGR HRSMDANVVS SSTIATYIDA LAKNASELEQ RSTAYEINNE  60
LELVFIKPPL ITLTNVVNIS TIQESFIRFT VTNKEGVKIR TKIPLSKVHG LDVKNVQLVD  120
AIDNIVWEKK SLVTENRLHK ECLLRLSTEE RHIFLDYKKY GSSIRLELVN LIQAKTKNFT  180
IDFKLKYFLG SGAQSKSSLL HAINHPKSRP NTSLEIEFTP RDNETVPYDE LIKELTTLSR  240
HIFMASPENV ILSPPINAPI KTFMLPKQDI VGLDLENLYA VTKTDGIPIT IRVTSNGLYC  300
YFTHLGYIIR YPVKRIIDSE VVVFGEAVKD KNWTVYLIKL IEPVNAINDR LEESKYVESK  360
LVDICDRIVF KSKKYEGPFT TTSEVVDMLS TYLPKQPEGV ILFYSKGPKS NIDFKIKKEN  420
TIDQTANVVF RYMSSEPIIF GESSIFVEYK KFSNDKGFPK EYGSGKIVLY NGVNYLNNIY  480
CLEYINTHNE VGIKSVVVPI KFIAEFLVNG EILKPRIDKT MKYINSEDYY GNQHNIIVEH  540
LRDQSIKIGD IFNEDKLSDV GHQYANNDKF RLNPEVSYFT NKRTRGPLGI LSNYVKTLLI  600
SMYCSKTFLD DSNKRKVLAI DFGNGADLEK YFYGEIALLV ATDPDADAIA RGNERYNKLN  660
SGIKTKYYKF DYIQETIRSD TFVSSVREVF YFGKFNIIDW QFAIHYSFHP RHYATVMNNL  720
SELTASGGKV LITTMDGDKL SKLTDKKTFI IHKNLPSSEN YMSVEKIADD RIVVYNPSTM  780
STPMTEYIIK KNDIVRVFNE YGFVLVDNVD FATIIERSKK FINGASTMED RPSTRNFFEL  840
NRGAIKCEGL DVEDLLSYYV VYVFSKRGGG GSGGGGSGGG GSMDEIVKNI REGTHVLLPF  900
YETLPELNLS LGKSPLPSLE YGANYFLQIS RVNDLNRMPT DMLKLFTHDI MLPESDLDKV  960
YEILKINSVK YYGRSTKADA VVADLSARNK LFKRERDAIK SNNHLTENNL YISDYKMLTF  1020
DVFRPLFDFV NEKYCIIKLP TLFGRGVIDT MRIYCSLFKN VRLLKCVSDS WLKDSAIMVA  1080
SDVCKKNLDL FMSHVKSVTK SSSWKDVNSV QFSILNNPVD TEFINKFLEF SNRVYEALYY  1140
VHSLLYSSMT SDSKSIENKH QRRLVKLLL                                   1169

SEQ ID NO: 7              moltype = RNA  length = 25
FEATURE                   Location/Qualifiers
misc_feature              1..25
                          note = Synthetic construct
misc_feature              1..25
                          note = Substrate RNA
misc_feature              1..25
                          note = 3' FAM
source                    1..25
                          mol_type = other RNA
                          organism = synthetic construct
misc_feature              1
                          note = 5' triphosphate
SEQUENCE: 7
gtagaacttc gtcgagtacg ctcaa                                       25

SEQ ID NO: 8              moltype = AA  length = 1132
FEATURE                   Location/Qualifiers
REGION                    1..1132
                          note = Synthetic construct
REGION                    1..1132
                          note = MISC_FEATURE - D1-Linker-D12 Polypeptide
VARIANT                   845
                          note = Xaa is a peptide linker from 2-100 residues in
                            length, wherein each position is independently any amino
                            acid
```

```
source              1..1132
                    mol_type = protein
                    organism = synthetic construct
SEQUENCE: 8
MDANVVSSST IATYIDALAK NASELEQRST AYEINNELEL VFIKPPLITL TNVVNISTIQ    60
ESFIRFTVTN KEGVKIRTKI PLSKVHGLDV KNVQLVDAID NIVWEKKSLV TENRLHKECL   120
LRLSTEERHI FLDYKKYGSS IRLELVNLIQ AKTKNFTIDF KLKYFLGSGA QSKSSLLHAI   180
NHPKSRPNTS LEIEFTPRDN ETVPYDELIK ELTTLSRHIF MASPENVILS PPINAPIKTF   240
MLPKQDIVGL DLENLYAVTK TDGIPITIRV TSNGLYCYFT HLGYIIRYPV KRIIDSEVVV   300
FGEAVKDKNW TVYLIKLIEP VNAINDRLEE SKYVESKLVD ICDRIVFKSK KYEGPFTTTS   360
EVVDMLSTYL PKQPEGVILF YSKGPKSNID FKIKKENTID QTANVVFRYM SSEPIIFGES   420
SIFVEYKKFS NDKGFPKEYG SGKIVLYNGV NYLNNIYCLE YINTHNEVGI KSVVVPIKFI   480
AEFLVNGEIL KPRIDKTMKY INSEDYYGNQ HNIIVEHLRD QSIKIGDIFN EDKLSDVGHQ   540
YANNDKFRLN PEVSYFTNKR TRGPLGILSN YVKTLLISMY CSKTFLDDSN KRKVLAIDFG   600
NGADLEKYFY GEIALLVATD PDADAIARGN ERYNKLNSGI KTKYYKFDYI QETIRSDTFV   660
SSVREVFYFG KFNIIDWQFA IHYSFHPRHY ATVMNNLSEL TASGGKVLIT TMDGDKLSKL   720
TDKKTFIIHK NLPSSENYMS VEKIADDRIV VYNPSTMSTP MTEYIIKKND IVRVFNEYGF   780
VLVDNVDFAT IIERSKKFIN GASTMEDRPS TRNFFELNRG AIKCEGLDVE DLLSYYVVYV   840
FSKRXMDEIV KNIREGTHVL LPFYETLPEL NLSLGKSPLP SLEYGANYFL QISRVNDLNR   900
MPTDMLKLFT HDIMLPESDL DKVYEILKIN SVKYYGRSTK ADAVVADLSA RNKLFKRERD   960
AIKSNNHLTE NNLYISDYKM LTFDVFRPLF DFVNEKYCII KLPTLFGRGV IDTMRIYCSL  1020
FKNVRLLKCV SDSWLKDSAI MVASDVCKKN LDLFMSHVKS VTKSSSWKDV NSVQFSILNN  1080
PVDTEFINKF LEFSNRVYEA LYYVHSLLYS SMTSDSKSIE NKHQRRLVKL LL          1132
```

VACCINIA CAPPING ENZYME COMPOSITIONS AND METHODS

CROSS-REFERENCE TO RELATED APPLICATIONS

This application is a divisional application of U.S. application Ser. No. 17/348,127 filed Jun. 15, 2021, which claims priority to U.S. Provisional Application No. 63/042,939 filed Jun. 23, 2020, the entire contents of which are hereby incorporated by reference.

REFERENCE TO AN ELECTRONIC SEQUENCE STATEMENT

This disclosure includes a Sequence Listing submitted electronically in xml format under file name "NEB-433-DIV-US.xml" created on Sep. 7, 2023, and having a size of 20.0 KB. The Sequence Listing is incorporated herein in its entirety by this reference.

BACKGROUND

The vaccinia RNA capping enzyme is a heterodimer consisting of a 97 kDa subunit encoded by the vaccinia virus D1R gene (GeneID:3707562; UniProtKB ID: YP 232988.1) and a 33-kDa subunit encoded by the vaccinia virus D12L gene (GeneID:3707515; UniProtKB ID: YP 232999.1). D1 is a catalytic subunit, which has RNA-triphosphatase, RNA guanylyltransferase and RNA N7-guanine methyltransferase enzymatic activities (Cong and Shuman 1993; Niles and Christen 1993; Higman and Niles 1994; Mao and Shuman 1994; Gong and Shuman 2003), whereas regulatory D12 subunit itself has no known enzymatic activity, but stimulates significantly the RNA N7-guanine methyltransferase activity of the D1 subunit (Higman, Bourgeois et al. 1992; Higman, Christen et al. 1994; Mao and Shuman 1994).

SUMMARY

The present disclosure relates to compositions, methods, and/or kits for producing vaccinia capping enzyme. For example, a vaccinia capping enzyme fusion transcript (e.g., a polynucleotide template for a fusion protein) may comprise, in a 5' to 3' direction: (a) a sequence encoding a D1 subunit, (b) a linker (e.g., an 1D2A linker, a sequence encoding a flexible linker or a cleavable linker), and (c) a sequence encoding a D12 subunit. The present disclosure further relates to compositions comprising a vaccinia capping enzyme fusion transcript. A D1 subunit encoded by a vaccinia capping enzyme fusion transcript may have an amino acid sequence having at least 90% identity to positions 24 to 867 of SEQ ID NO: 1 and/or may have an amino acid sequence having at least 90% identity to SEQ ID NO: 1. A linker may have an amino acid sequence having at least 90% identity to SEQ ID NO: 3 or an amino acid sequence having at least 90% identity to SEQ ID NO: 5. A D12 subunit encoded by a vaccinia capping enzyme fusion transcript may have an amino acid sequence having at least 90% identity to SEQ ID NO: 2. A vaccinia capping enzyme fusion transcript may comprise a cap and/or a polyA tail. In some embodiments, a vaccinia capping enzyme fusion transcript may be introduced or otherwise present (e.g., transcribed from an expression cassette) in a cell. A cell having a vaccinia capping enzyme fusion transcript may comprise equimolar amounts of D1 and D12. A cell may comprise a catalytically active vaccinia capping enzyme. A vaccinia capping enzyme fusion protein in a cell may have an amino acid sequence at least 90% identical to SEQ ID NO: 4 or at least 90% identical to SEQ ID NO: 6 or at least 90% identical to SEQ ID NO: 8.

The present disclosure related to vaccinia capping enzyme fusions and compositions comprising such fusion proteins. For example, a vaccinia capping enzyme fusion enzyme (e.g., included in a composition) may comprise, in an N-terminal to C-terminal orientation, a D1 subunit, a linker, and a D12 subunit. The present disclosure further provides expressible polynucleotides (e.g., DNA) encoding vaccinia capping enzyme fusions.

A D1 subunit of a vaccinia capping enzyme fusion may have an amino acid sequence having at least 90% identity to positions 24 to 867 of SEQ ID NO: 1 and/or may have an amino acid sequence having at least 90% identity to SEQ ID NO: 1. A linker of a vaccinia capping enzyme fusion may have an amino acid sequence having at least 90% identity to SEQ ID NO: 3 or an amino acid sequence having at least 90% identity to SEQ ID NO: 5. A D12 subunit of a vaccinia capping enzyme fusion may have an amino acid sequence having at least 90% identity to SEQ ID NO: 2.

In some embodiments, methods of producing a vaccinia capping enzyme (e.g., a catalytically active vaccinia capping enzyme) may comprise contacting a vaccinia capping enzyme fusion transcript with a suitable expression system. A vaccinia capping enzyme fusion transcript may comprise, in a 5' to 3' orientation, (i) a sequence encoding D1, (ii) a sequence encoding a linker, and (iii) a sequence encoding D12. In some embodiments, an expression system may be a yeast expression system comprising, for example, *Kluyveromyces lactis* or *Pichia pastoris*. A vaccinia capping enzyme fusion transcript may comprise a cap and/or a polyA tail. Producing a vaccinia capping enzyme may comprise contacting a bacteria or a yeast comprising a DNA encoding a vaccinia capping enzyme fusion or fusion transcript operably linked to an expression control sequence with suitable media under conditions and for a time sufficient to permit such bacteria or yeast to produce the vaccinia capping enzyme fusion transcript and/or the vaccinia capping enzyme fusion encoded by the vaccinia capping enzyme fusion transcript. The produced vaccinia capping enzyme may comprise equimolar quantities of D1 and D12.

A kit for capping a transcript, according to some embodiments, may comprise a composition comprising a vaccinia capping enzyme fusion and, optionally, a mastermix. A kit may further comprise one or more additional enzymes including, for example, a decapping enzyme. A kit for producing a vaccinia capping enzyme fusion may comprise (a) a vaccinia capping enzyme fusion transcript comprising, in a 5' to 3' orientation, (i) a sequence encoding D1, (ii) a sequence encoding a linker, and (iii) a sequence encoding D12 and (b) an expression system (e.g., a cell-free, a bacterial, or a yeast expression system).

DETAILED DESCRIPTION

Figure 1A:
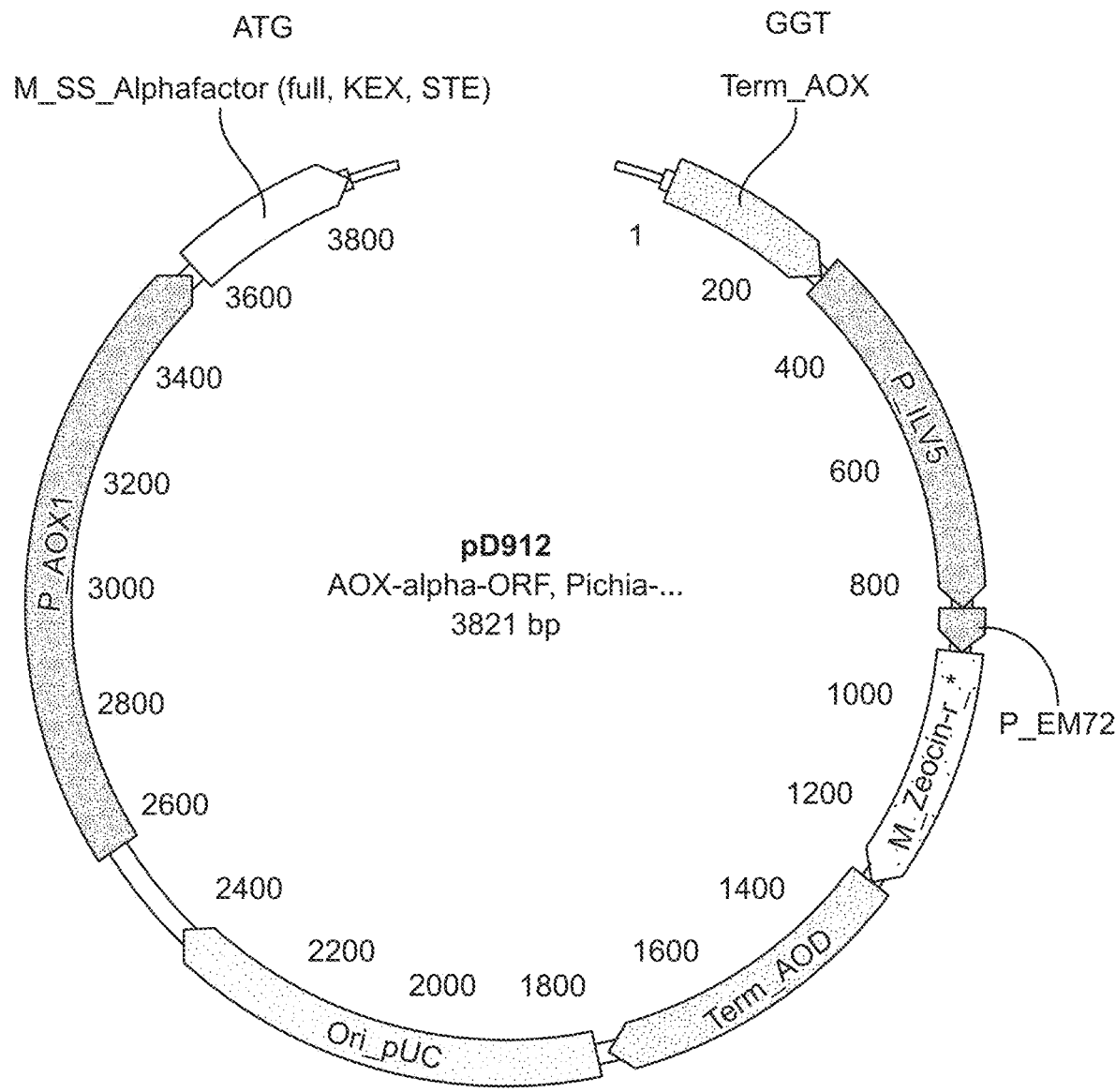
FIG. 1A shows a general map of the yeast expression vector pD912 (ATUM, formerly DNA 2.0) used to assemble plasmids used containing D1-1D2A-D12 and D1-GS-D12 fusion constructs.
Figure 1B:
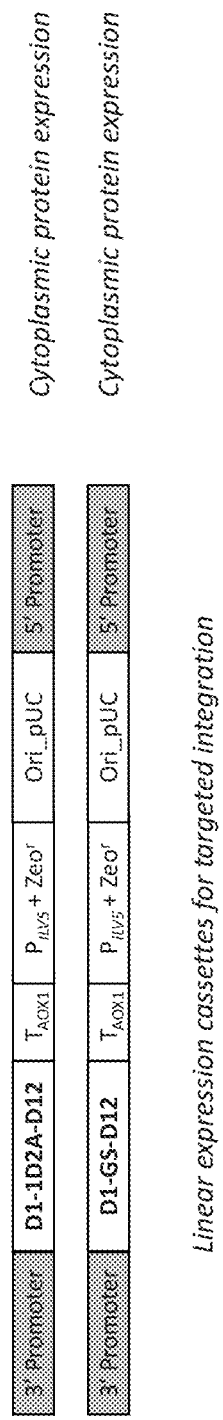
FIG. 1B shows a schematic of the linear integrative expression cassettes, which were prepared by PCR from the assembled plasmids as a DNA template. The assembled plasmids and linear cassettes had the following design: GAP or AOX1 promoter, followed by the amino-terminal His-tagged D1 and un-tagged D12 ORFs, fused with either 1D2A or GS linker (D1-1D2A-D12 and D1-GS- D12); AOX1 terminator sequence ($T_{AOX1}$); zeocin resistance gene under control of the ILV5 promoter ($P_{ILV5}$+Zeo$^r$); the sequence of the origin of replication (Ori_pUC); flanking sequences for the targeted integration (3' Promoter fragment contains the sequence of the actual promoter).

Aspects of the present disclosure can be further understood in light of the embodiments, section headings, figures, descriptions and examples, none of which should be construed as limiting the entire scope of the present disclosure in any way. Accordingly, the claims set forth below should be construed in view of the full breadth and spirit of the disclosure.

Each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

Unless otherwise defined, all technical and scientific terms used herein have the same meaning as commonly understood by one of ordinary skill in the art to which this disclosure belongs. Still, certain terms are defined herein with respect to embodiments of the disclosure and for the sake of clarity and ease of reference.

Sources of commonly understood terms and symbols may include: standard treatises and texts such as Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); Singleton, et al., Dictionary of Microbiology and Molecular biology, 2d ed., John Wiley and Sons, New York (1994), and Hale & Markham, the Harper Collins Dictionary of Biology, Harper Perennial, N.Y. (1991) and the like.

As used herein and in the appended claims, the singular forms "a" and "an" include plural referents unless the context clearly dictates otherwise. For example, the term "a protein" refers to one or more proteins, i.e., a single protein and multiple proteins. It is further noted that the claims can be drafted to exclude any optional element. As such, this statement is intended to serve as antecedent basis for use of such exclusive terminology as "solely," "only" and the like in connection with the recitation of claim elements or use of a "negative" limitation.

Numeric ranges are inclusive of the numbers defining the range. All numbers should be understood to encompass the midpoint of the integer above and below the integer i.e., the number 2 encompasses 1.5-2.5. The number 2.5 encompasses 2.45-2.55 etc. When sample numerical values are provided, each alone may represent an intermediate value in a range of values and together may represent the extremes of a range unless specified.

In the context of the present disclosure, "active" refers to catalytic activity. For example, an active vaccinia capping enzyme fusion has at least detectable RNA-triphosphatase activity, at least detectable RNA guanylyltransferase activity, and at least detectable RNA N7-guanine methyltransferase activity.

In the context of the present disclosure, "cap" refers to natural caps, such as $^7$mG, and to a compound of the general formula R3p$_3$N1-p-N(x), where R3 is a guanine, adenine, cytosine, uridine or analogs thereof (e.g., N$^7$-methylguanosine; m$^7$G), p$_3$ is a triphosphate linkage, N1 and Nx are ribonucleosides, x is 0-8 and p is, independently for each position, a phosphate group, a phosphorothioates, phosphorodithioate, alkylphosphonate, arylphosphonate, or a N-phosphoramidate linkage. Cap analogs are added at the 5' end of an RNA transcript in a process called co-transcriptional capping to yield a 5' capped RNA.

In the context of the present disclosure, "D1" and "D1 subunit" refer to the 97 kDa VCE subunit encoded by the vaccinia virus D1R gene (GeneID:3707562; UniProtKB ID: YP 232988.1) having RNA-triphosphatase, RNA guanylyltransferase and RNA N7-guanine methyltransferase enzymatic activities. D1 may have an amino acid sequence sharing at least 90%, at least 92%, at least 94%, at least 96%, or at least 98% identity with SEQ ID NO: 1. D1 optionally may comprise a histidine tag, for example, at its N-terminus. Unless otherwise indicated, D1 refers to the whole subunit. D1 optionally may comprise one or more modified amino acids (e.g., hydroxylated, phosphorylated, myristoylated, palmitoylated, isoprenylated, sulfated, ubiquitinated, glycosylated (e.g., N-linked, O-linked), lipoylated, acetylated, alkylated (e.g., methylated), biotinylated, amidated, oxidized (e.g., cysteines forming a S—S bond) or reduced).

In the context of the present disclosure, "D12" and "D12 subunit" refer to the 33 kDa VCE subunit encoded by the vaccinia virus D12L gene (GeneID:3707515; UniProtKB ID: YP 232999.1) and capable of enhancing the RNA N7-guanine methyltransferase activity of the D1 subunit (e.g., beyond such activity of D1 in the absence of D12). D12 may have an amino acid sequence sharing at least 90%, at least 92%, at least 94%, at least 96%, or at least 98% identity with SEQ ID NO: 1. Unless otherwise indicated, D12 refers to the whole subunit. D1 and D12 subunits may be associated with each other with or without a covalent linker. D12 optionally may comprise one or more modified amino acids (e.g., hydroxylated, phosphorylated, myristoylated, palmitoylated, isoprenylated, sulfated, ubiquitinated, glycosylated (e.g., N-linked, O-linked), lipoylated, acetylated, alkylated (e.g., methylated), biotinylated, amidated, oxidized (e.g., cysteines forming a S—S bond) or reduced).

In the context of the present disclosure, "expression system" refers to systems for producing a protein from a polynucleotide template comprising components to produce the protein according to an RNA template (e.g., enzymes, amino acids, an energy source), (optionally) components to produce the RNA template according to another RNA template or a DNA template (e.g., enzymes, nucleotides, an energy source). An expression system may comprise a bacterial (e.g., *Escherichia coli*) or yeast (e.g., *Kluyveromyces lactis* or *Pichia pastoris*) expression system in which the protein is encoded by an RNA or DNA template within an expression cassette, a plasmid or other expression vector. An expression system may comprise a viral expression system in which the protein is encoded by an RNA or DNA template (e.g., in an expression cassette) within a viral genome or viral expression vector. Examples of cell-free expression systems may include or comprise cell extracts of *Escherichia coli* S30, rabbit reticulocytes or wheat germ; PURE-EXPRESS® (New England Biolabs, Ipswich, MA). An expression cassette may comprise, in some embodiments, an expression control sequence (e.g., promoter), a coding sequence encoding the gene product (e.g., protein) of interest (e.g., a vaccinia capping enzyme fusion), and/or one or more termination sequences (e.g., terminators). An expression control sequence (e.g., promoter) may comprise any promoter operative in a desired expression system, including, for example, a GAP promoter, an AOX1 promoter, a T7 promoter, a T5 promoter, a Ptac promoter, a Ptrc promoter, ParaBAD promoter, a PrhaBAD promoter, a Tet promoter or a PhoA phosphate-starvation promoter.

In the context of the present disclosure, "fusion" refers to two or more polypeptides, subunits, or proteins covalently joined to one another (e.g., by a peptide bond). For example, a protein fusion may refer to a non-naturally occurring polypeptide comprising the protein covalently joined to a reporter protein. Alternatively, where a protein comprises two separate polypeptide subunit chains, a fusion may comprise a non-naturally occurring combined polypeptide chain comprising the two subunits joined directly to each other by a peptide bond or through a peptide linker.

In the context of the present disclosure, "GS" refers to flexible linkers comprising glycine and serine, for example, repeats of glycine and serine residues $(Gly_xSer_y)_n$, where independently, x=1, 2, 3, 4, 5, 6, 7, 8, 9, 10, or more than 10, y=1, 2, 3, 4, 5, 6, 7, 8, 9, 10, or more than 10, and n=1, 2, 3, 4, 5, 6, 7, 8, 9, 10, or more than 10. For example, x, y, and/or n independently may be in a range of 1-3, 2-4, 3-5, 4-6, 5-7, 6-8, 7-9, 8-10, 9-11, 10-12, or more.

In the context of the present disclosure, "1D2A" refers to a polypeptide comprising, in an N-terminal to C-terminal direction, 14 amino acid residues of the capsid protein 1D, and a 2A proteinase of picornaviruses including, for example, 2A proteinases of rhinoviruses. An 1D2A may comprise a 2A proteinase derived from foot and mouth disease virus.

In the context of the present disclosure, "peptide linker" refers to a peptide, oligopeptide, polypeptide chain comprising two or more (e.g., 2-25, 20-40, 5-50, 10-100, >100) amino acids adapted to form a link (e.g., via peptide bonds at the N-terminal and C-terminal ends of the linker) between subunits of vaccinia capping enzyme. A peptide linker may comprise one or more modified amino acids (e.g., hydroxylated, phosphorylated, myristoylated, palmitoylated, isoprenylated, sulfated, ubiquitinated, glycosylated (e.g., N-linked, O-linked), lipoylated, acetylated, alkylated (e.g., methylated), biotinylated, amidated, oxidized (e.g., cysteines forming a S—S bond) or reduced). Examples of peptide linkers include GS and 1D2A.

In the context of the present disclosure, "non-naturally occurring" refers to a polynucleotide, polypeptide, carbohydrate, lipid, or composition that does not exist in nature.

Such a polynucleotide, polypeptide, carbohydrate, lipid, or composition may differ from naturally occurring polynucleotides polypeptides, carbohydrates, lipids, or compositions in one or more respects. For example, a polymer (e.g., a polynucleotide, polypeptide, or carbohydrate) may differ in the kind and arrangement of the component building blocks (e.g., nucleotide sequence, amino acid sequence, or sugar molecules). A polymer may differ from a naturally occurring polymer with respect to the molecule(s) to which it is linked. For example, a "non-naturally occurring" protein may differ from naturally occurring proteins in its secondary, tertiary, or quaternary structure, by having a chemical bond (e.g., a covalent bond including a peptide bond, a phosphate bond, a disulfide bond, an ester bond, and ether bond, and others) to a polypeptide (e.g., a fusion protein), a lipid, a carbohydrate, or any other molecule. Similarly, a "non-naturally occurring" polynucleotide or nucleic acid may contain one or more other modifications (e.g., an added label or other moiety) to the 5'-end, the 3' end, and/or between the 5'- and 3'-ends (e.g., methylation) of the nucleic acid. A "non-naturally occurring" composition may differ from naturally occurring compositions in one or more of the following respects: (a) having components that are not combined in nature, (b) having components in concentrations not found in nature, (c) omitting one or components otherwise found in naturally occurring compositions, (d) having a form not found in nature, e.g., dried, freeze dried, crystalline, aqueous, and (e) having one or more additional components beyond those found in nature (e.g., buffering agents, a detergent, a dye, a solvent or a preservative). All publications, patents, and patent applications cited, listed, or otherwise mentioned in this specification are herein incorporated by reference to the same extent as if each individual publication, patent, or patent application was specifically and individually indicated to be incorporated by reference.

In the context of the present disclosure, "polynucleotide linker sequence" refers to a polynucleotide sequence that links the 3' end of one subject polynucleotides to the 5' end of another polynucleotide. A polynucleotide linker sequence may encode a polypeptide linker (e.g., a GS linker) and/or may allow, cause or promote ribosome skipping during translation.

In the context of the present disclosure, "transcript" refers to a polynucleotide template for a polypeptide. A transcript may comprise RNA (e.g., ssRNA), a cap or cap analog, and/or a polyA tail. A transcript may be capable of translation in a cell (e.g., a bacterial cell and/or a yeast cell). For example, a transcript may be or comprise mRNA. A fusion transcript may comprise polynucleotide templates for two or more polypeptides in a single polynucleotide.

The potential for mRNA vaccines to transform the treatment of infectious diseases has gained considerable traction since it was first proposed. Manufacturing may be cell-free and scalable. Once the sequence of a desired immunogen is provided, the time required to produce clinical batches of vaccine might be weeks instead of months. Such rapid production may limit or even avert widespread outbreaks.

Production of stable mRNA capable of efficient translation upon introduction to a subject may require an appropriate cap structure. Vaccinia virus, like most viruses, has a robust set of tools to co-opt host cell machinery for the production of viral proteins. One such tool is the vaccinia capping enzyme, which forms a Cap 0 structure (m7Gppp5' N) at the 5' end of uncapped RNA molecules through its RNA triphosphatase, guanylyltransferase, and guanine methyltransferase activities. In cells, capping viral transcripts allows them to be transcribed by the infected cells.

Other transcripts may be capped rapidly in vitro in the presence of the vaccinia capping enzyme, reaction buffer, GTP, and the methyl donor, SAM. Capping by VCE may be nearly 100% efficient and all capped structures may be added in the proper orientation (e.g., compared to co-transcriptional addition of some cap analogs). Capping by vaccinia capping enzyme may be desired or even required for production of an effective RNA vaccine. For example, a suitable cap structure may impact the stability and translatability of an RNA vaccine.

Production of active vaccinia capping enzyme for cell-free vaccine production can be challenging. Properties of VCE may impede production (e.g., high capacity production) and use of the enzyme. For example, efforts to express the vaccinia virus D1R gene in bacteria and yeast as a means to produce and recover the 97 kDa subunit result in low yields. Without limiting any embodiment to any specific mechanism of action, this appears to be due, at least in part, to the insolubility and/or hydrophobicity of the 97 kDa subunit. In addition, in vitro assembly of the small and large subunits into a heterodimer may yield an enzyme with little to no catalytic activity. Separately produced subunits may not be present in an appropriate ratio or conformation to efficiently or productively bind to one another and/or bind to substrates.

A 2A sequence derived from foot-and-mouth disease virus can be used as an alternative strategy to generate different proteins derived from a fusion protein precursor (Osborn et al. 2005). A region of 18 amino acid residues from 2A followed by a proline promoted "cleavage" in a co-translational manner using a nonproteolytic mechanism termed "ribosome skipping" (Donnelly, Luke et al. 2001). Addition of 14 amino acid residues of the capsid protein 1D to the N-terminal of 2A increased the activity of self-processing up to 99% (Donnelly, Hughes et al. 2001). An artificial polyprotein precursor comprising this 1D2A sequence flanked by reporter genes was efficiently processed into separate polypeptides in tested eukaryotic cells, including *Pichia pastoris* (Lee et al. 2012; Rasala et al. 2012; Chng et al. 2015; Sun et al. 2012; de Amorim Aradjo et al. 2015). After processing, the 1D2A peptide remains as a C-terminal extension of the upstream protein and all products downstream of 2A contain a proline residue at the N-terminal (Ryan et al. 1991; Donnelly, Luke et al. 2001; De Felipe et al. 2003).

Linkers used in the construction of multidomain proteins may comprise repeats of glycine and serine residues $(Gly_xSer_y)_n$. The combination of flexible (Gly) and hydrophilic (Ser) residues in these linkers has multiple advantages, since it may not interfere with a folding and function of the fusion proteins. The absence of protease-sensitive sites of the common eukaryotic proteases in the Gly-Ser linker sequences potentially contributes to the stability of the linker of the chimeric proteins (Crasto and Feng 2000).

The present disclosure relates to compositions, methods, and kits for producing active vaccinia capping enzyme. For example, compositions may comprise a vaccinia capping enzyme fusion comprising (e.g., in a single polypeptide chain) a D1 subunit, a D12 subunit, and a linker (e.g., a flexible linker, a cleavable linker) positioned between the carboxy terminal end of the D1 subunit and the amino terminal end of the D12 subunit. A vaccinia capping enzyme fusion may comprise, for example, in an N-terminal to C-terminal direction, (a) a polypeptide having a sequence at least 90% identical to positions 24 to 867 of SEQ ID NO:1, (b) a linker having at least 90% identity to SEQ ID NO: 3 or at least 90% identity to SEQ ID NO: 5, and (c) a polypeptide having a sequence at least 90% identity to SEQ ID NO: 2. For example, a composition may comprise a vaccinia capping enzyme fusion comprising a polypeptide having an amino acid sequence at least 90% (e.g., at least 92%, at least 95%, at least 97%) identical to SEQ ID NO: 4 or at least 90% (e.g., at least 92%, at least 95%, at least 97%) identical to SEQ ID NO: 6 or at least 90% (e.g., at least 92%, at least 95%, at least 97%) identical to SEQ ID NO: 8. A vaccinia capping enzyme fusion may be stable as a single polypeptide chain and/or may have a desired susceptibility to cleavage (e.g., by a protease at a location in or near the linker).

Compositions may comprise, in some embodiments, a vaccinia capping enzyme fusion transcript (e.g., a single polynucleotide chain) comprising a sequence encoding a vaccinia capping enzyme fusion. For example, a vaccinia capping enzyme fusion transcript may comprise, in a 5' to 3' direction: (a) a sequence encoding a D1 subunit, (b) a linker (e.g., an 1D2A linker, a sequence encoding a flexible linker or a cleavable linker), and (c) a sequence encoding a D12 subunit. For example, a composition may comprise a vaccinia capping enzyme fusion transcript may encode a polypeptide having an amino acid sequence at least 90% identical to SEQ ID NO: 4 or at least 90% identical to SEQ ID NO: 6 or at least 90% identical to SEQ ID NO: 8. A vaccinia capping enzyme fusion transcript, according to some embodiments, may comprise a cap (e.g., a 5' Cap 0). Compositions optionally may comprise one or more of the components set forth below for kits. In some embodiments, a composition may be glycerol-free, may be dry (e.g., as a result of lyophilization), and/or may be aqueous.

Methods for production of vaccinia capping enzyme may comprise, for example, contacting a vaccinia capping enzyme fusion polynucleotide comprising, in a 5' to 3' orientation, (a) a sequence encoding a polypeptide having at least 90% identity to D1, (b) a sequence encoding a linker having at 90% identity to 1D2A (SEQ ID NO: 3) or at least 90% identity to GS (SEQ ID NO: 5), and (c) at least 90% identity to D12, with an expression system (e.g., a bacterial expression system, a yeast expression system, a viral expression system or a cell-free expression system). A method may optionally comprise capping a vaccinia capping enzyme fusion polynucleotide with a cap or a cap analog.

Kits

The present disclosure further relates to kits including a vaccinia capping enzyme fusion. For example, a kit may include a vaccinia capping enzyme fusion and an uncapped ribonucleic acid, dNTPs, rNTPs, primers, other enzymes (e.g., decapping enzymes, polymerases, other enzymes, or both), buffering agents, or combinations thereof. A vaccinia capping enzyme fusion may be included in a storage buffer (e.g., comprising glycerol and a buffering agent). A kit may include a reaction buffer which may be in concentrated form, and the buffer may contain additives (e.g. glycerol), salt (e.g. KCl), reducing agent, EDTA or detergents, among others. A kit comprising dNTPs may include one, two, three or all four of dATP, dTTP, dGTP and dCTP. A kit comprising rNTPs may include one, two, three of all four or rATP, rUTP, rGTP and rCTP. A kit may further comprise one or more modified nucleotides. A kit may optionally comprise one or more primers (random primers, bump primers, exonuclease-resistant primers, chemically-modified primers, custom sequence primers, or combinations thereof). One or more components of a kit may be included in one container for a single step reaction, or one or more components may be contained in one container, but separated from other components for sequential use or parallel use. The contents of a kit may be formulated for use in a desired method or process.

A kit is provided that contains: (i) A vaccinia capping enzyme fusion; and (ii) a buffer. A vaccinia capping enzyme fusion may have a lyophilized form or may be included in a buffer (e.g., a storage buffer or a reaction buffer in concentrated form). A kit may contain a vaccinia capping enzyme fusion in a mastermix suitable for receiving and capping a template ribonucleic acid. A vaccinia capping enzyme fusion may be a purified enzyme so as to contain no other detectable enzyme activities. The reaction buffer in (ii) and/or storage buffers containing a vaccinia capping enzyme fusion in (i) may include non-ionic, ionic e.g. anionic or zwitterionic surfactants, denaturants, and/or crowding agents. A kit may include a vaccinia capping enzyme fusion and the reaction buffer in a single tube or in different tubes.

A subject kit may further include instructions for using the components of the kit to practice a desired method. The instructions may be recorded on a suitable recording medium. For example, instructions may be printed on a substrate, such as paper or plastic, etc. As such, the instructions may be present in the kits as a package insert, in the labeling of the container of the kit or components thereof (i.e., associated with the packaging or sub-packaging) etc. Instructions may be present as an electronic storage data file residing on a suitable computer readable storage medium (e.g., a CD-ROM, a flash drive). Instructions may be provided remotely using, for example, cloud or internet resources with a link or other access instructions provided in or with a kit.

EXAMPLES

Some specific embodiments may be illustrated by one or more of the examples provided herein.

Example 1: Expression of 2A Fusion Construct Produces Active Heterodimeric VCE A. Plasmids and Linear Expression Cassettes The pD912(GAP)/D1-1D2A-D12 plasmid comprises sequences encoding vaccinia mRNA capping enzyme D1 and D12 subunits, arranged to be expressible as a single polypeptide. A sequence encoding a D1 subunit having an amino-terminal His-tag (SEQ ID NO:1) was fused to a sequence encoding the amino-terminus of the un-tagged D12 subunit (SEQ ID NO:2) via a sequence encoding a 33 amino acid residue 1D2A linker (SEQ ID NO:3).

The plasmid was synthesized and assembled using PCR and in vitro DNA assembly methods. The pD912(GAP) was prepared from pD912(AOX) vector by replacing 462 bp long AOX1 promoter sequence with 483 bp long DNA fragment containing Pichia pastoris GAP promoter. The pD912(GAP) vector backbone without the sequence encoding for secretion leader was amplified by PCR. The ORFs of D1 and D12 were amplified from pET23bVCE plasmid using PCR method. All amplified DNA fragments were purified by gel extraction and assembled into the plasmid using NEBuilder HiFi DNA Assembly Mix. The resulting pD912(GAP)/D1-1D2A-D12 plasmid contained the self-processive D1-1D2A-D12 construct under control of the constitutive GAP promoter for the cytoplasmic expression in Pichia pastoris. The non-naturally occurring VCE protein sequence encoded by pD912(GAP)/D1-1D2A-D12 plasmid corresponds to SEQ ID NO:4.

Another variant of a heterodimeric D1-1D2A-D12 fusion was generated by assembling a construct into the pD912 (AOX) vector. The resulting pD912(AOX1)/D1-1D2A-D12 plasmid contained a fusion construct under control of the methanol inducible AOX1 promoter for the cytoplasmic expression in Pichia pastoris.

Another active heterodimeric construct of vaccinia mRNA capping enzyme subunits was generated by fusion of D1 and D12 via flexible non-cleavable linker (Gly-Gly-Gly-Gly-Ser)$_3$ SEQ ID NO:5. The genes of D1 and D12 were amplified from pET23bVCE plasmid using PCR method. The pD912(GAP) vector backbone minus the sequence encoding for secretion leader was amplified by PCR. All amplified DNA fragments were purified by gel extraction and assembled into the plasmid using NEBuilder HiFi DNA Assembly Mix. The resulting pD912(GAP)/D1-GS-D12 plasmid contained D1-GS-D12 construct under control of the constitutive GAP promoter for the cytoplasmic expression in Pichia pastoris. The protein sequence encoded by pD912(GAP)/D1-GS-D12 plasmid corresponds to SEQ ID NO:6.

A linear expression cassette was PCR amplified from the assembled plasmids (FIG. 1A). The amplified expression cassette was purified by gel extraction and used for yeast transformation.

B. Yeast Transformation and Integration

Pichia pastoris aox1Δ (MutS) (ATUM, formerly DNA 2.0) strain was used in all experiments under this Example. Pichia pastoris electrocompetent cells were prepared by a lithium acetate/DTT method (Wu and Letchworth, 2004). 0.2 μg of a purified linear expression cassette was introduced into Pichia pastoris electrocompetent cells (electroporation conditions: 1.5 KV, 25 μF and 200 Ohm; 0.2 mm cuvette) followed by selection of transformants by growth on yeast peptone dextrose (YPD) agar medium supplemented with 1 M sorbitol and 500 μg/mL Zeocin (Teknova) for 3-4 days at 30° C.

For the identification of transformants by PCR, genomic DNA was isolated from each colony selected for testing using a lithium acetate/sodium dodecyl sulfate (LiOAc/SDS) method (Looke et al., 2011). PCR was used to identify transformants having an integrated expression cassette. The amplified genomic DNA fragments were purified and used to verify the sequence of the integrated construct.

C. Yeast Culture Conditions and Expression

For constructs containing GAP promoter, Pichia pastoris transformants were grown at 30° C. in 5-25 mL of yeast medium (1% yeast extract, 2% peptone, 1.34% yeast nitrogen base (YNB) without amino acids, 0.0004% biotin, 10 mM potassium phosphate, pH 6.0) supplemented with 2% glycerol as the carbon source. After 48 hours, the cells and spent culture media were harvested.

For constructs containing AOX1 promoter, Pichia pastoris transformants were grown to near saturation (OD=20 at 600 nm) at 30° C. in 10 mL of yeast medium (1% yeast extract, 2% peptone, 1.34% yeast nitrogen base, 0.0004% biotin, 10 mM potassium phosphate, pH 6.0) supplemented with 1% glycerol as the carbon source. Cells were harvested and resuspended in 4 ml of the same medium with 0.5% (v/v) methanol instead of glycerol and incubated for 48 hours.

D. Protein Purification and Analysis

To prepare cell lysate, cells were resuspended in 20 mM Tris-HCl, pH7.5 buffer, containing 100 mM NaCl. The cells disrupted using a high pressure homogenizer at 30 KPsi (Dyhydromatics), and the cell lysate pre-cleared by centrifugation at 17000×g for 45 minutes. The cell lysates and spent culture media were analyzed by SDS-PAGE on 10-20% polyacrylamide gel, followed by western blotting with His-tag antibodies (Thermofisher) or mouse monoclonal antibodies against D1 or D12 subunits (GenScript).

Purification of the expressed recombinant fusion proteins from cell lysates was performed using the NEBExpress Ni Spin columns according to manufacturer's recommendations (NEB).

E. In Vitro mRNA Capping Assay

In vitro capping reactions were carried out in a 10 μL reaction containing 1× capping buffer (50 mM Tris pH 8.0, 5 mM KCl, 1 mM MgCl$_2$, 1 mM DTT) supplemented with 0.1 mM S-adenosylmethionine, 0.5 mM GTP, 500 nM substrate RNA (5'-pppGUAGAACUUCGUCGAGUACG-CUCAA[FAM]-3' (SEQ ID NO:7), Bio-Synthesis, Inc.), and purified enzyme at 37° C. for 30 minutes. Reactions were stopped by adding 10 μL of quenching solution (20 mM EDTA, 2% SDS). Reactions were diluted in nuclease-free water to reach a final substrate concentration of 5 nM before capillary electrophoresis on either an Applied Biosystems 3130x1 Genetic Analyzer (16 capillary array) or an Applied Biosystems 3730x1 Genetic Analyzer (96 capillary array) using GeneScan 120 LIZ dye Size Standard (Applied Biosystems). Reaction products were analyzed using PeakScanner software (Thermo Fisher Scientific).

F. Results: Active Enzyme was Produced

Western blot analysis of the transformants expressing cytoplasmic heterodimer D1-1D2A-D12 indicated that the recombinant fusion protein is expressed in *Pichia pastoris* cytoplasm as a soluble protein. The results indicate, that the self-processive D1-1D2A-D12 is only partially processed, since D1 and D12 subunits were present in both fused and individual forms (FIG. 2).

Figure 2:
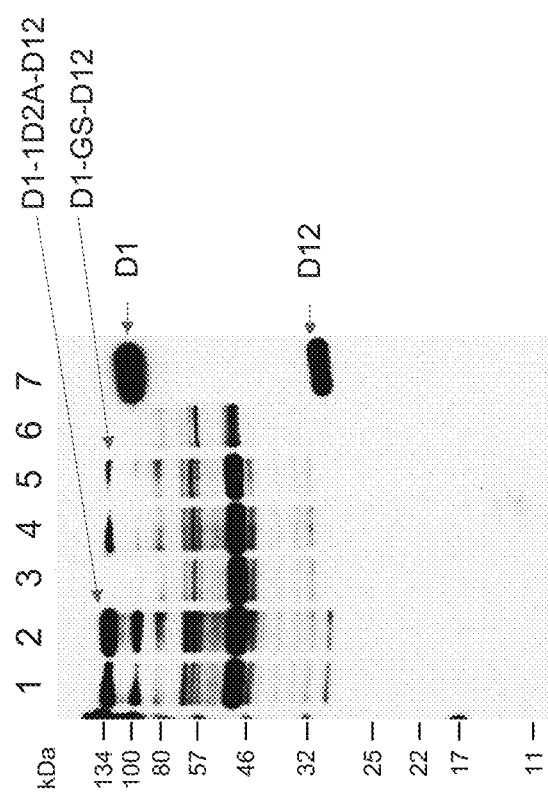
FIG. 2 shows the cytoplasmic expression of the D1-1D2A-D12 and D1-GS-D12 fusion proteins in *Pichia pastoris* cells transformed with constructs containing GAP promoter. The transformants were grown in the medium with 2% glycerol at 30° C. The cells were harvested after 48 hours incubation. The cell lysates were prepared by high pressure homogenization and analyzed by analyzed by SDS-PAGE on 10-20% polyacrylamide gel, followed by western blotting with His-tag antibodies and mouse monoclonal antibodies against D12 subunit. Lanes 1,2—cell lysates of *Pichia* transformants #1 and #2 expressing D1-1D2A-D12; lanes 3,6—control *Pichia* cell lysates; lanes 4,5—cell lysates of *Pichia* transformants #1 and #2 expressing D1-GS-D12; lane 7—recombinant VCE (NEB).
Figure 3:
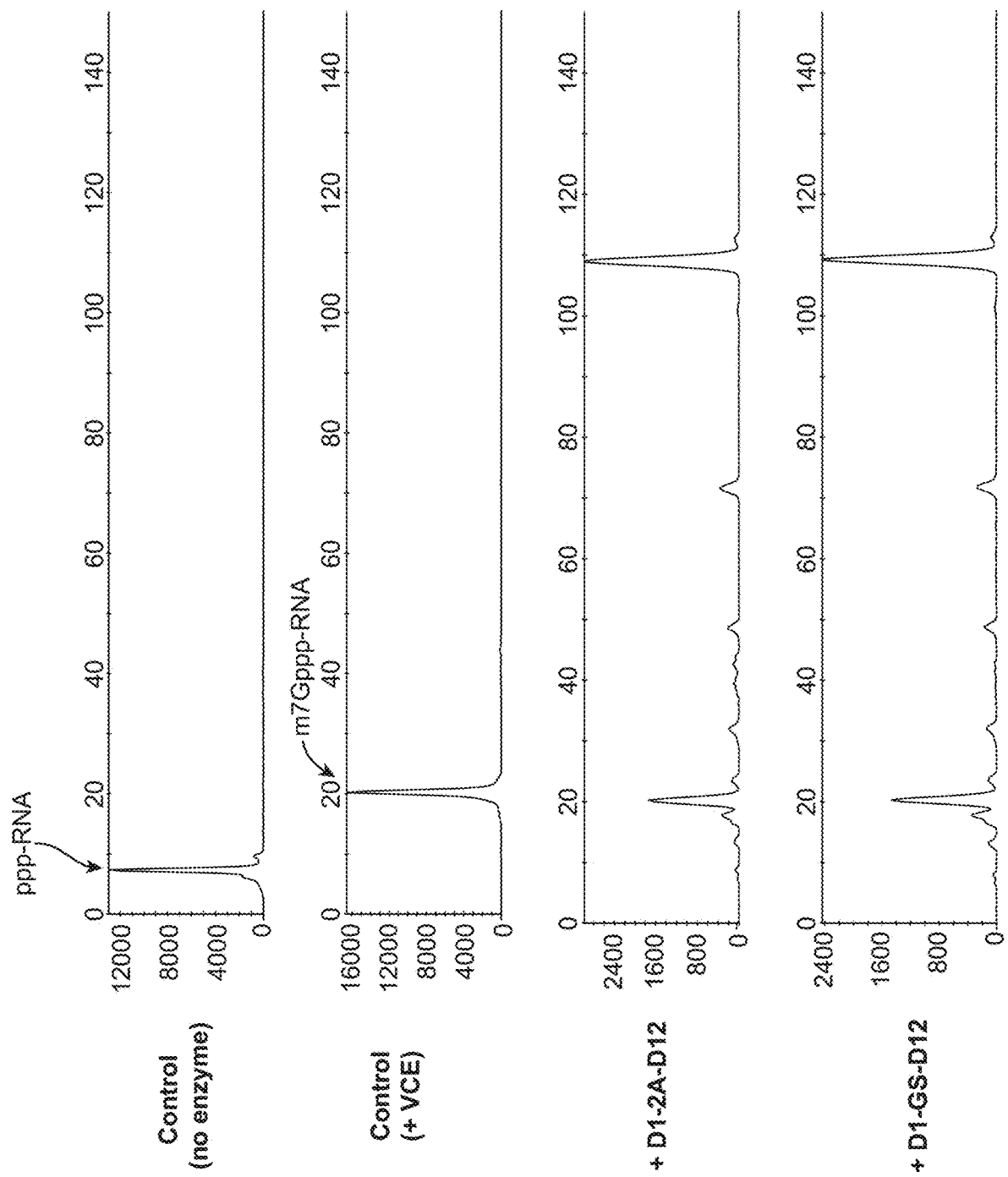
FIG. 3 shows the activity of the partially purified D1-1D2A-D12 and D1-GS-D12 proteins. The recombinant fusion proteins were purified from the cell lysates using the NEBExpress nickel spin columns. The activity of the purified proteins was assayed using an in vitro mRNA capping assay as described in Example 1E.

The cytoplasmic heterodimer D1-GS-D12 fusion protein containing flexible linker is also expressed as a single polypeptide (FIG. 2). Partially purified D1-1D2A-D12 and D1-GS-D12 were tested for mRNA capping activity. Both recombinant proteins were active (FIG. 3).

REFERENCES

Cong, P. and S. Shuman (1993). "Covalent catalysis in nucleotidyl transfer. A KTDG motif essential for enzyme-GMP complex formation by mRNA capping enzyme is conserved at the active sites of RNA and DNA ligases." *J Biol Chem* 268(10): 7256-60.

Niles, E. G. and L. Christen (1993). "Identification of the vaccinia virus mRNA guanyltransferase active site lysine." *J Biol Chem* 268(33): 24986-9.

Higman, M. A. and E. G. Niles (1994). "Location of the S-adenosyl-L-methionine binding region of the vaccinia virus mRNA (guanine-7-)methyltransferase." *J Biol Chem* 269(21): 14982-7.

Mao, X. and S. Shuman (1994). "Intrinsic RNA (guanine-7)methyltransferase activity of the vaccinia virus capping enzyme D1 subunit is stimulated by the D12 subunit. Identification of amino acid residues in the D1 protein required for subunit association and methyl group transfer." *J Biol Chem* 269(39): 24472-9.

Gong, C. and S. Shuman (2003). "Mapping the active site of vaccinia virus RNA triphosphatase." *Virology* 309(1): 125-34.

Higman, M. A., N. Bourgeois, et al. (1992). "The vaccinia virus mRNA (guanine-N-7-)-methyltransferase requires both subunits of the mRNA capping enzyme for activity." *J Biol Chem* 267(23): 16430-7.

Higman, M. A., L. A. Christen, et al. (1994). "The mRNA (guanine-7)methyltransferase domain of the vaccinia virus mRNA capping enzyme. Expression in *Escherichia coli* and structural and kinetic comparison to the intact capping enzyme." *J Biol Chem* 269(21): 14974-81.

Osborn M J, Panoskaltsis-Mortari A, Mcelmurry R T, Bell S K, Vignali D A A, Ryan M D, Wilber A C, McIvor R S, Tolar J, Blazar B R. A picornaviral 2A-like sequence-based tricistronic vector allowing for high-level therapeutic gene expression coupled to a dual-reporter system. Mol Ther. 2005; 12:569-574.

Donnelly M L L, Luke G, Mehrotra A, Li X, Hughes L E, Gani D, Ryan M D. b Analysis of the aphthovirus 2A/2B polyprotein 'cleavage' mechanism indicates not a proteolytic reaction, but a novel translational effect: a putative ribosomal 'skip' J Gen Virol. 2001; 82:1013-1025.

Donnelly M L L, Hughes L E, Luke G, Mendoza H, ten Dam E, Gani D, Ryan M D. The 'cleavage' activities of foot-and-mouth disease virus 2A site-directed mutants and naturally occurring '2A-like' sequences. J Gen Virol. 2001; 82:1027-1041. doi: 10.1099/0022-1317-82-5-1027.

Lee D S, Lee K H, Jung S, Jo E J, Han K H, Bae H J. Synergistic effects of 2A-mediated polyproteins on the production of lignocellulose degradation enzymes in tobacco plants. J Exp Bot. 2012; 63:4797-4810.

Rasala B A, Lee P A, Shen Z, Briggs S P, Mendez M, Mayfield S P. (2012). Robust expression and secretion of Xylanase1 in *Chlamydomonas reinhardtii* by fusion to a selection gene and processing with the FMDV 2A peptide. PLoS One. 7:e43349.

Chng J, Wang T, Nian R, Lau A, Hoi K M, Ho S C, Gagnon P, Bi X, Yang Y. (2015). Cleavage efficient 2A peptides for high level monoclonal antibody expression in CHO cells. MAbs. 7:403-412.

Sun Y F, Lin Y, Zhang J H, Zheng S P, Ye Y R, Liang X X, Han S Y. (2012). Double *Candida antarctica* lipase B co-display on *Pichia pastoris* cell surface based on a self-processing foot-and-mouth disease virus 2A peptide. Appl Microbiol Biotechnol. 96:1539-1550.

de Amorim Arúdjo, J., Ferreira, T. C., Rubini, M. R., Duran, A. G., De Marco, J. L., de Moraes, L. M., & Torres, F. A. (2015). Coexpression of cellulases in *Pichia pastoris* as a self-processing protein fusion. *AMB Express*, 5(1), 84.

Ryan M D, King A M Q, Thomas G P. (1991). Cleavage of foot-and-mouth disease virus polyprotein is mediated by residues located within a 19 amino acid sequence. *J Gen Virol.* 72:2727-2732.

De Felipe P, Hughes L E, Ryan M D, Brown J D. (2003). Co-translational, intraribosomal cleavage of polypeptides by the foot-and-mouth disease virus 2A peptide. J Chem. 278:11441-11448.

Crasto, C. J., & Feng, J. A. (2000). LINKER: a program to generate linker sequences for fusion proteins. *Protein engineering*, 13(5), 309-312.

Wu, S., & Letchworth, G. J. (2004). High efficiency transformation by electroporation of *Pichia pastoris* pretreated with lithium acetate and dithiothreitol. *BioTechniques*, 36(1), 152-154.

Lõoke, M., Kristjuhan, K., & Kristjuhan, A. (2011). Extraction of genomic DNA from yeasts for PCR-based applications. *BioTechniques*, 50(5), 325-328.

What is claimed is:

1. A vaccinia capping enzyme fusion transcript comprising, in a 5' to 3' direction: (a) a sequence encoding a D1 subunit, (b) a sequence encoding a linker, and (c) a sequence encoding a D12 subunit, wherein the linker has at least 90% identity to SEQ ID NO: 3.

2. A composition comprising a vaccinia capping enzyme fusion transcript, wherein the vaccinia capping enzyme fusion transcript comprises, in a 5' to 3' direction:
   (a) a sequence encoding a D1 subunit;
   (b) a sequence encoding a linker; and
   (c) a sequence encoding a D12 subunit, wherein the linker has at least 90% identity to SEQ ID NO: 3.

3. A composition according to claim 2, wherein the D1 subunit has an amino acid sequence having at least 90% identity to positions 24 to 867 of SEQ ID NO: 1.

4. A composition according to claim 2, wherein the D1 subunit has an amino acid sequence having at least 90% identity to SEQ ID NO: 1.

5. A composition according to claim 2, wherein the D12 subunit has an amino acid sequence having at least 90% identity to SEQ ID NO: 2.

6. A composition according to claim 2, wherein the vaccinia capping enzyme fusion transcript further comprises (d) a cap.

7. A cell comprising the composition according to claim 2.

8. A cell according to claim 7, further comprising equimolar amounts of the D1 subunit and the D12 subunit.

9. A cell according to claim 7, further comprising an active vaccinia capping enzyme fusion protein.

10. A cell according to claim 8, wherein the vaccinia capping enzyme fusion protein has an amino acid sequence at least 90% identical to SEQ ID NO: 4 or at least 90% identical to SEQ ID NO: 6 or at least 90% identical to SEQ ID NO: 8.

11. A method for producing an active vaccinia capping enzyme comprising:
   contacting
      (a) a vaccinia capping enzyme fusion transcript comprising, in a 5' to 3' orientation,
         (i) a sequence encoding D1, (ii) a sequence encoding a linker having at least 90% identity to SEQ ID NO: 3, and
         (iii) a sequence encoding D12; with
      (b) an expression system.

12. A method according to claim 11, wherein the expression system is a yeast expression system.

13. A method according to claim 12, wherein the yeast is *Kluyveromyces lactis* or *Pichia pastoris*.

14. A cell according to claim 7, wherein the cell is a *Kluyveromyces lactis* cell or a *Pichia pastoris* cell.

* * * * *